United States Patent [19]

Aslam et al.

[11] Patent Number: 5,300,698
[45] Date of Patent: Apr. 5, 1994

[54] PROCESS FOR THE PREPARTION OF 1,3,5-TRIS(4'-HYDROXYARYL)BENZENE

[75] Inventors: Mohammad Aslam, Corpus Christi, Tex.; William Basinger, Decatur, Ga.

[73] Assignee: Hoechst Celanese Corporation, Somerville, N.J.

[21] Appl. No.: 68,460

[22] Filed: May 27, 1993

[51] Int. Cl.$^5$ ............................................. C07C 39/16
[52] U.S. Cl. ..................................... 568/720; 568/718
[58] Field of Search ..................... 568/718, 720, 727

[56] References Cited

U.S. PATENT DOCUMENTS 3,644,538  7/1972  Starnes, Jr. .................... 568/720
4,394,496  7/1983  Schrader ........................ 528/098
4,992,598  2/1991  Strutz et al. .................... 568/720

FOREIGN PATENT DOCUMENTS 1252388  11/1971  United Kingdom ............... 568/720

*Primary Examiner*—Werren B. Lone
*Attorney, Agent, or Firm*—P. S. Kalyanaraman

[57] ABSTRACT

Novel 4-substituted acetophenone anils and methods for preparing 1,3,5-tris(4'-hydroxyphenyl)benzenes from 4-substituted acetophenones such as 4-hydroxyacetophenones or, from substituted 4-hydroxyacetophenone-anils such as 4-hydroxyacetophenone-anil by reacting the 4-substituted acetophenone or corresponding anil with an aniline derivative.

24 Claims, No Drawings

PROCESS FOR THE PREPARTION OF 1,3,5-TRIS(4'-HYDROXYARYL)BENZENE

CROSS REFERENCE TO RELATED APPLICATIONS

Reference is hereby made to the commonly owned and concurrently filed application of Aslam et al. entitled Process for the Preparation of 1,3,5-tris(4'-hydroxyphenyl)benzene and its Derivatives and Intermediate Compounds Serial No.07/891,167, filed Jan. 08, 1992, and the application of Hilton entitled Epoxidation Products of 1,3,5-(4'-hydroxyphenyl)benzenes, Ser. No. 07/819,166, filed Jan. 08, 1992.

FIELD OF THE INVENTION

This invention relates to a process for preparing 1,3,5-tris(4'-hydroxyphenyl)benzene (THPB) and related compounds from 4-hydroxyacetophenones (4-HAP). Condensation of three acetophenone molecules produces an aromatic nucleus to provide 1,3,5-trisphenyl benzenes.

BACKGROUND OF THE INVENTION 1,3,5-tris(4'-hydroxyphenyl)benzene falls into the class of compounds known as trisphenyls. Trisphenyls have been recognized as useful intermediates in the preparation of more complex organic structures. For example, resins are readily prepared by a reacting trisphenyls with formaldehyde, acid anhydrides and more importantly with epichlorohydrin. Epoxide resins prepared from such compounds exhibit low shrinkage, extraordinary hardness, chemical inertness, outstanding mechanical strength, and a variety of beneficial features. See, for example, U.S. Pat. No. 4,394,496; and, the above-referenced application of Hilton.

1,3,5-tris(4'-hydroxyphenyl)benzene (THPB) molecules are particularly useful in their ability to stabilize polycarbonates. This is accomplished via a three site rigid $D_{3h}$ crosslink. THPB molecules may also be used as crosslinking agents in epoxy resins. See, for example, *Chem. Abstracts.*, 66, 3004C.

THPB was reported in *Beilstein*, E II 6, 1115 (1921). The treatment of 4-methoxyacetophenone (4-MAP) with sulfuric acid produced 1,3,5-tris(4'-methoxyphenyl)benzene (4-MAP trimer or TMPB)(20% yield). This compound was demethylated with concentrated hydrochloric acid to yield THPB.

THPB was also reported in *Chimia*, 12, 143 (1958) and in *Chimia*, 13, 105 (1959) as formed by the trimerization of 4-haloacetophenone, where the halogen is either bromine or chlorine, in the presence of potassium pyrosulfate and sulfuric acid. This reaction results in 1,3,5-tris(4'-halophenyl)benzenes. These halogen-containing trimers were treated with sodium hydroxide and converted to THPB.

M. H. Karger and Y. Mazur, *J. Org. Chem*, 36, 540 (1971), reported that anisole and acetyl methanesulfonate, affords 4-MAP (46% yield) and TMPB (41% yield). Subsequent to anisole acetylation, trimerization is catalyzed by methanesulfonic acid.

R. E. Lyle, E. J. DeWitt, N. M. Nichols, and W. Cleland, *J. Amer. Chem. Soc.*, 75, 5959 (1953), report the trimerization of substituted acetophenones, i.e., 4-MAP to TMPB (54% yield), by an alcoholic hydrogen chloride solution, after four months at room temperature.

G. P. Sharnin, I. E. Moisak, E. E. Gryazin, *Zhurnal Prikladnoi Khimii*, 43, 1642 (1970), report the trimerization of 4-MAP to TMPB (27% yield) using a mixture of potassium pyrosulfate and sulfuric acid. See also, A. F. Odel et al., *J. Amer. Chem. Soc.*, 36, 81 (1913).

P. Milart and J. Cioslowski, *Synthesis*, p. 328-29 (1984) relate to the use of 4-alkoxyacetophenones to prepare 4-alkoxyacetophenone anils which are condensed to form 1,3,5-tris(4'-alkoxyphenyl)benzenes. However, the reference does not suggest using 4-hydroxyacetophenone (4-HAP) or substituted 4-hydroxyacetophenones to produce 4-hydroxyacetophenone-anil (4-HAP-anil) or substituted 4-hydroxyacetophenone-anils, which may be then condensed to form 1,3,5-tris(4'-hydroxyphenyl)benzene or substituted 1,3,5-tris(4'-hydroxyphenyl)benzenes. In fact, the reference teaches the conversion of 4-hydroxyacetophenone to 4-alkoxyacetophenone before converting to the corresponding anil and thereafter trimerizing the anil. This is consistent with earlier teachings which describe unsuccessful efforts to trimerize hydroxyacetophenone. See, for example, G. P. Sharnin et al., supra, see also R. E. Lyle et al., supra. Its is also consistent with prior teachings that 1,3,5-tris(4'-hydroxyphenyl)benzene is produced by hydrolyzing the corresponding 4'-alkoxy substituted compound which is prepared using 4-alkoxyacetophenone. See, for example, Beilstein, E II 6, 1115 (1921). Moreover, P. Milart et al. fail to teach or suggest a one step process for trimerizing 4-HAP.

U.S. Pat. No. 3,458,473, issued Jul. 29, 1969 to Starnes et al. is directed to the preparation of various hindered trisphenyls prepared by the cyclotrimerization of an acetylphenol precursor.

U.S. Pat. No. 3,644,538 issued Feb. 22, 1972 to W. H. Starnes, discloses that both 3'-alkyl- and 3',5'-dialkyl-4'-hydroxyacetophenones can be trimerized to the corresponding triarylbenzenes with anhydrous HCl and triethyl orthoformate and ethanol. Trimerization of unsubstituted 4-HAP is not suggested or disclosed. Starnes also fails to teach or suggest trimerizing substituted or unsubstituted 4-HAP-anil.

German Patent 258,929 to Zimmerman et al., issued Aug. 10, 1988 is directed to methods for the production of 1,3,5-tris(triarylbenzene) compounds. These compounds are reacted by combining 2,4,6-triaryl pyrylium salts with carboxylic acid anhydride in the presence of a basic condensing agent. The reaction of Zimmerman utilizes triaryl pyrylium carboxylic anhydride.

Elmorsy et al., "The Direct Production of Tri- and Hexa-Substituted Benzenes from Ketones Under Mild Conditions," Tetrahedron Letters, Vol. 32, No. 33, pp. 4175-4176 (1991) report the treatment of aryl benzenes with tetrachlorosilane in ethanol to yield 1,3,5-triarylbenzenes. However, Elmorsy et al. fail to teach or suggest trimerizing 4-hydroxyacetophenone, a 4-hydroxyacetophenone derivative, or a 4-substituted-oxyacetophenone by contacting such a compound with a halosilane, as in the present invention. Indeed, it is believed that trimerizing a hydroxyacetophenone such as 4-hydroxyacetophenone or a 4-hydroxyacetophenone derivative, is not disclosed or suggested by Elmorsy et al. because of the belief that the hydroxy group would interfere with the reaction, for example, react with the tetrachlorosilane. See, e.g,, Sharin et al., supra, which illustrate why it was believed, before now, that direct trimerization of hydroxyacetophenone was not feasible. Accordingly, Elmorsy et al. fail to teach or suggest the present invention.

SUMMARY OF THE INVENTION

In accordance with this invention, a process is provided for the preparation of 1,3,5-tris(4'-hydroxyphenyl)benzene (THPB) and related compounds from 4-hydroxyacetophenone (4-HAP) and corresponding substituted 4-hydroxyacetophenones. Until now, the direct trimerization of 4-hydroxyacetophenone (4-HAP) to 1,3,5-tris(4'-hydroxyphenyl)benzene (THPB) was believed to be not feasible.

The inventive reaction provides a novel approach for the large scale synthesis of 1,3,5-tris(4'-hydroxyphenyl)-benzene or related compounds. In a broad sense, the present invention provides a process for the production of 1,3,5-tris(4'-hydroxyphenyl)benzene or its related compounds by contacting the corresponding substituted 4-hydroxyacetophenone with aniline or an aniline derivative to form the 4-hydroxyacetophenone-anil, and, contacting the 4-hydroxyacetophenone-anil with a catalytic amount of an acid catalyst, preferably an anilinium salt, such as anilinium hydrochloride, anilinium hydrobromide, anilinium sulfate, anilinium tosylate and the like, to form 1,3,5-tris(4'-hydroxyphenyl)benzene or its related compounds. The term "aniline derivative" refers to substituted aniline wherein the substituents are on the aromatic ring of the aniline and are selected from the group consisting of $C_1-C_6$ alkyl, $C_1-C_6$ alkoxy, and halo. The scope of the invention also provides for the use of naphthylamine and naphthylamine derivative in place of aniline and aniline derivative respectively, and of naphthylaminium salt in place of the anilinium salt, as is known to those skilled in the art.

More specifically, the process comprises treating 4-hydroxyacetophenone or other substituted 4-hydroxyacetophenones with aniline, preferably by refluxing, and preferably in the presence of a solvent such as toluene to produce 4-hydroxyacetophenone-anil (4-HAP-anil) or the corresponding substituted 4-hydroxyacetophenone-anil. The 4-hydroxyacetophenone-anil or substituted 4-hydroxyacetophenone-anil is trimerized in the presence of an acid catalyst, e.g., HCl, HBr, $H_2SO_4$ or the like, preferably an acidic anilinium salt such as anilinium hydrochloride, anilinium hydrobromide, anilinium sulfate or anilinium tosylate to produce 1,3,5-tris(4'-hydroxyphenyl)benzene or the corresponding substituted 1,3,5-tris(4'-hydroxyphenyl)benzene. The present invention also provides a process for the production of 1,3,5-tris(4'-hydroxyphenyl) benzene comprising contacting 4-hydroxyacetophenone-anil with anilinium hydrochloride, under reaction conditions.

The inventive process is based on the following general reaction in which three acetophenone molecules, e.g., 4-hydroxyacetophenone or substituted 4-hydroxyacetophenone molecules, are condensed to provide a 1,3,5-tris(4'-hydroxyphenyl)benzene or substituted 1,3,5-tris(4'-hydroxyphenyl)benzene.

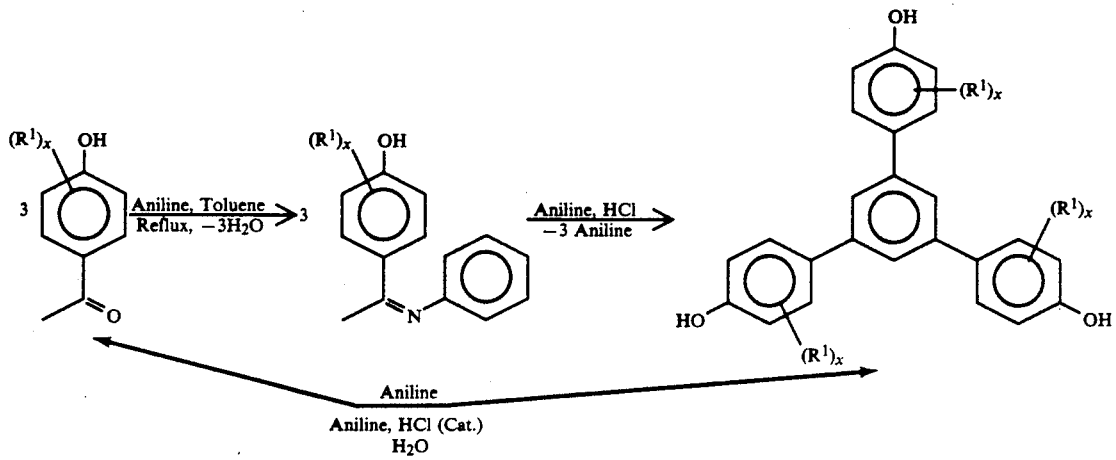

In one embodiment, the reaction can be carried out in one step, without the isolation of 4-hydroxyacetophenone-anil or a substituted 4-hydroxyacetophenone-anil. In the reaction, the 4-hydroxyacetophenone or a substituted 4-hydroxyacetophenone is treated with the aniline in the presence of an acid catalyst to form the 1,3,5-tris(4'-hydroxyphenyl)benzene or a substituted 1,3,5-tris(4'-hydroxyphenyl)benzene.

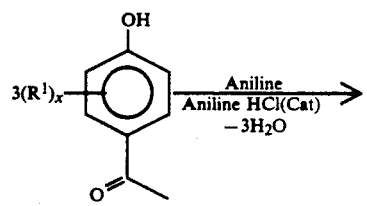

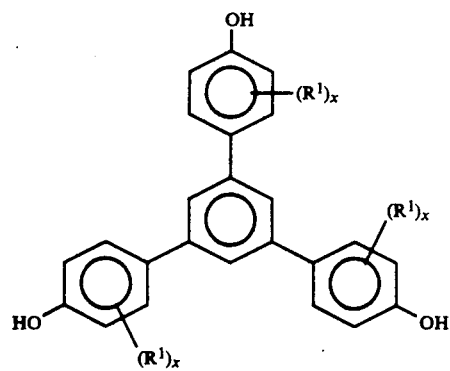

In each of the above reaction schemes, $R^1$ is hydrogen, an alkyl group such as an alkyl group having from 1 to about 12 carbon atoms preferably a $C_1-C_5$ lower alkyl, such as methyl or ethyl, a cycloalkyl of from about 3 to about 6 carbon atoms, phenyl (including mono or polysubstituted phenyl, e.g., with halogen and/or nitro), halogen, such as Br, Cl, I or F, $NO_2$ or sulfonyl (alkyl or aromatic). The alkyl group of the alkyl sulfonyl is preferably an alkyl group having from 1 to about 12 carbon atoms, more preferably a $C_1$-$C_5$ lower alkyl, for instance, a $C_1$-$C_5$ lower alkyl substituted by one or more halogen and/or nitro groups. The aromatic of the aromatic sulfonyl is preferably phenyl, or an alkyl substituted aromatic such as an aromatic substituted by one or more lower alkyl groups, for instance, tolyl, xylyl, cumenyl or the like, or an aromatic substituted by one or more halogen and/or nitro groups.

In addition, the acetophenone molecule can have from one to four $R^1$ substituents on it (e.g., at any or all of the 2, 3, 5 and 6 positions); and, these multiple $R^1$ substituents can be the same or different. Thus, x can be an integer from 1 to 4, and, when x is greater than 1, the $R^1$ substituents can be the same or different.

In the inventive process, it has been found, surprisingly, that the 4-hydroxyacetophenone carbonyl group is converted to the aniline imine, which undergoes cyclotrimerization readily in the presence of the acidic, preferably anilinium salt, condensing agent which is regenerated in the process.

A significant advantage of the process of the invention is that the process may be carried out in a single step and provides for the production of THPB and its derivatives, without using a number of reaction steps and reagents which were necessary in the past.

DETAILED DESCRIPTION

An embodiment of the present invention is exemplified by the following general reaction in which three acetophenone molecules are condensed to provide a 1,3,5-trisaryl benzene:

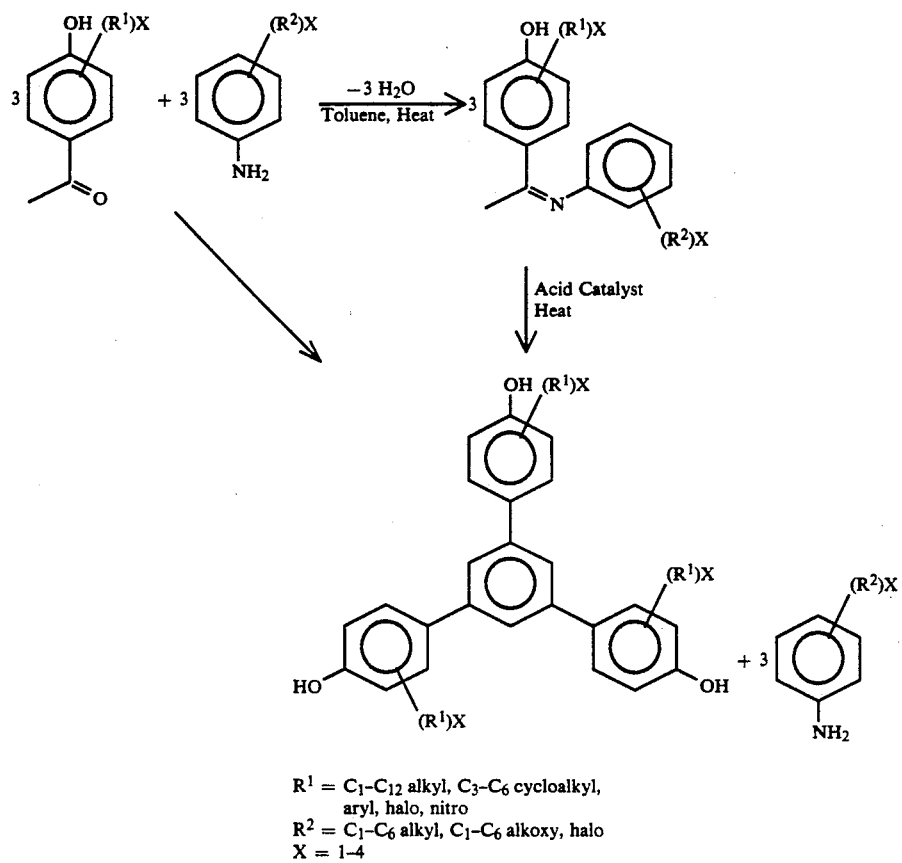

$R^1$ = $C_1$-$C_{12}$ alkyl, $C_3$-$C_6$ cycloalkyl, aryl, halo, nitro
$R^2$ = $C_1$-$C_6$ alkyl, $C_1$-$C_6$ alkoxy, halo
X = 1-4

Another embodiment of the present invention is illustrated by the preparation of THPB from 4-HAP by the following reaction scheme:

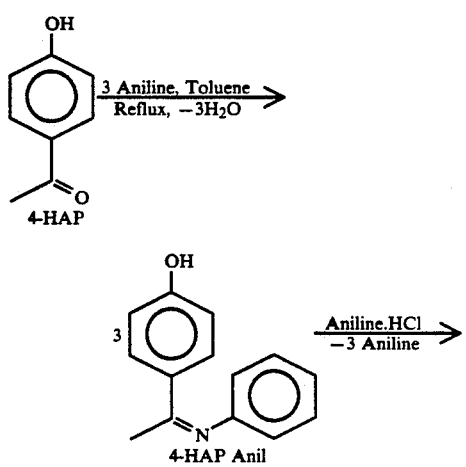

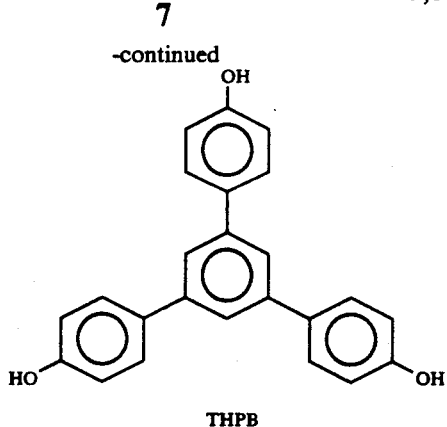

THPB

Yet another embodiment of the present invention is illustrated by the following one step process to prepare THPB from 4-HAP.

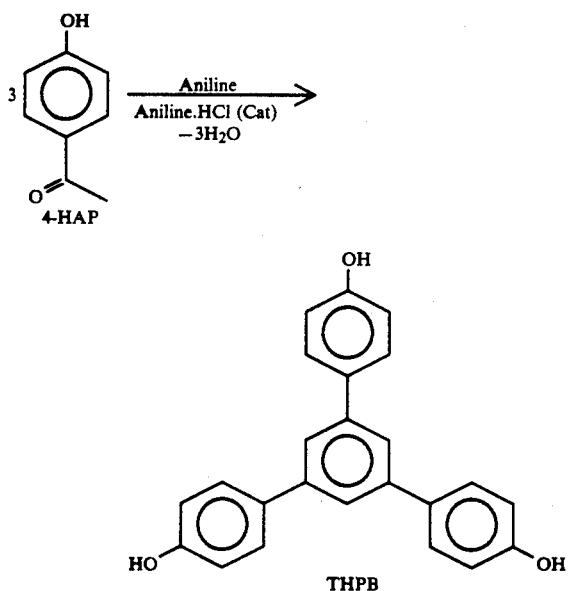

In this one step process, the 1,3,5-trisaryl benzene such as THPB is prepared, via a conversion from the corresponding substituted 4-hydroxyacetophenone such as 4-HAP without the isolation of the 4-hydroxyacetophenone-anil such as 4-HAP-anil. Generally, three acetophenone molecules, in the presence of sufficient quantities of aniline and anilinium hydrochloride, and optionally in the presence of a solvent, for example, a non-polar solvent such as toluene, are condensed to provide the corresponding 1,3,5-trisaryl benzene. Reaction conditions can be varied but generally are ambient pressure and temperatures and times which do not significantly decompose the reactants and/or product, and, which provide a satisfactory yield of desired product. Typical reaction times are about 0.5 to 8 hours, and typical reaction temperatures range from about 500° to about 2200C.

Alternatively, the substituted 4-HAP can be contacted with an aniline to yield the anil; the contacting is preferably in the presence of a solvent. Anilinium hydrochloride is thereafter added in a sufficient quantity and the solvent removed by distillation. These reaction mixtures are each heated at a temperature and for a time, again, so as to not result in significant decomposition of reactants and/or product, and, so as to obtain a satisfactory yield of desired product. For contacting the substituted 4-HAP with an aniline derivative to yield the anil, the reaction conditions are typically times of 2 to 24 hours and temperatures of 800° to 160° C.; and, for contacting the anil with the acidic anilinium salt (e.g., anilinium hydrochloride), the reaction conditions are typically times of 0.25 to 4 hours and temperatures of 1800 to 2200° C.

The 1,3,5-trisaryl benzene, for instance, THPB, is recovered from the reaction mixture by, for instance, cooling the reaction mixture and precipitating the product; addition of a suitable solvent, for example, a non-polar solvent such as toluene, in a suitable amount, to separate out oil, decanting the supernatant liquid to leave an oily residue, and adding a suitable solvent, for example, a non-polar solvent such as hexane, to the oily residue to cause the THPB to precipitate is also possible. The 1,3,5-trisaryl benzene such as THPB is preferably recrystallized to increase its purity. Whether the 1,3,5-trisarylbenzene is prepared from corresponding acetophenone or acetophenone-anil as illustrated above, the starting material is to be used in at least 3 molar ratios with respect to the quantity of the end product.

It is within the ambit of the skilled artisan to select appropriate quantities of the reactants, aniline, anilinium salts and solvent and to select appropriate reaction times and temperatures. The selection of appropriate reaction times and temperatures depends upon various factors, such as the quantity of reactants. Furthermore, in this Description, wherever aniline is described as a reactant, it is to be presumed that aniline derivative, as explained above, may be substituted as a reactant.

When the aniline and anilinium salt are aniline and anilinium hydrochloride respectively, it is preferred that the number of moles of aniline present during the reaction be at least equal to or more than the number of moles of the substituted 4-hydroxyacetophenone present. The ratio of the number of moles of aniline to the number of moles of the substituted 4-hydroxyacetophenone (e.g., aniline: 4-hydroxyacetophenone) is about 1.0:1.0 to about 10:1. The aniline: substituted 4-hydroxyacetophenone mole ratio is most preferably about 2:1.

Anilinium hydrochloride is present in sufficient quantities to catalyze the cyclotrimerization and the regeneration of aniline. In the reaction mixture, the ratio of the number of moles of anilinium hydrochloride to the number of moles of the 4-hydroxyacetophenone such as 4-HAP is preferably about 0.01:1 to about 0.25:1 (or about 1:4 to about 1:100).

When the aniline: 4-hydroxyacetophenone mole ratio is about 2:1, the ratio of the number of moles of anilinium hydrochloride to the number of moles of 4-hydroxyacetophenone is about 0.02:1 to about 0.1:1, preferably about 0.04:1.0 (or, about 1.0:10 to about 1.0:50, preferably about 1.0:25). Likewise, a preferred ratio of the number of moles of aniline initially added to the number of moles of anilinium hydrochloride is about 1:0.02, when the aniline: 4-hydroxyacetophenone mole ratio is about 2:1.

As to the solvents used in the reaction, the substituted 4-hydroxyacetophenone and aniline are preferably contacted in the presence of a solvent such as toluene. A preferred solvent to add to the cooled reaction mixture is also toluene, and, it is preferably added in about the same amount used during the initial contacting. To precipitate the 1,3,5-tris(4'-hydroxyaryl)benzene from the oily residue, hexane is a preferred non-polar solvent, and, it is preferably present in excess.

Other suitable solvents used during the reaction of the 4-hydroxyacetophenone in the presence of the aniline include xylene; during the oil separation include pentane; and, during the precipitation of the 1,3,5-tris(4-hydroxyaryl)benzene may be pentane, cyclohexane, and the like.

The aniline and aniline derivatives utilized to promote the formation of the 4-hydroxyacetophenone-anil are aniline, p-methyl aniline, nitro aniline, chloro aniline, and the like. Acids such as HCl, HBr, H$_2$SO$_4$ and the like may be used to catalyze the condensation to the 1,3,5-tris(4'-hydroxyaryl)benzene; however, acids derived from aniline, especially from the aniline used to form the anil, are preferred. Suitable acidic anilinium salts include aniline•HCl, aniline•HBr, aniline•sulfate, aniline•tosylate, or the like.

In another embodiment, the 4-hydroxyacetophenone-anil is prepared, isolated and then utilized to form the corresponding 1,3,5-trisaryl benzene. According to this process, in an initial reaction, a suitable quantity of the 4-hydroxyacetophenone such as 4-HAP is contacted with aniline, optionally in the presence of a solvent, e.g., a non-polar solvent such as toluene, under reaction conditions, to form the corresponding anil compound. The reaction conditions are temperature, time and pressure conditions which do not cause significant decomposition of reactants and/or product, and, which obtain a satisfactory yield of desired product. Typical reaction conditions include temperatures of about 1500° C. to about 180° C. times of about 2 to about 24 hours and pressures of about 50 mm to about 760 mm Hg. For example, the reaction may be carried out under reflux for up to 17 hours at a pressure achieved using a condenser and Dean Stark trap. Conditions may vary depending upon the scale of the reaction (quantities of reactants) and other factors usually considered by the skilled artisan.

The number of moles of aniline present is an amount at least equal to or preferably exceeding the number of moles of the 4-hydroxyacetophenone present. The mole ratio of aniline: 4-hydroxyacetophenone ranges from about 1:1 to about 10:1, most preferably about 3.0:1.0. A preferred solvent for this reaction is toluene. This invention is not limited to the use of toluene as a solvent as other suitable solvents may also be employed, including xylene, cyclohexane and the like.

As the 4-hydroxyacetophenone and aniline are reacted, water from the reaction is collected by, for example, a trap via a condenser, and, after a sufficient time, the 4-hydroxyacetophenone-anil is recovered from the reaction mixture. For instance, when the reaction is complete, the reaction mixture is cooled after a period of time, for example, up to 17 hours and, then combined with a solvent, for example, a non-polar solvent such as hexane, to form an oily product, e.g. a yellowish-brown oily product in the case of 4-hydroxyacetophenone-anil, which separates out of the reaction mixture. The quantity of hexane used is preferably about 2.5 to about 500 moles per mole of the 4-hydroxyacetophenone initially added. Most preferably, the ratio is about 8.0:1.0. The oily product is recrystallized with a solvent, for example, a non-polar solvent such as hexane, to afford a solid. The recrystallization solvent is preferably used in an amount of the order mentioned above for the solvent utilized to separate the oily product from the cooled reaction mixture (e.g., on a small scale 3×200 ml). The solid is preferably recrystallized to afford a solid, e.g., 4-HAP-anil. Any suitable solvent or solvent combination, e.g., non-polar solvents or combinations of relatively non-polar solvents may be employed for the recrystallization. Ether/hexane is one suggested solvent combination for the recrystallization. However, the invention is not limited to these recovery steps for obtaining the anil compound from the reaction mixture as other effective procedures or solvents may be used, such other solvents including pentane, cyclohexane and the like.

4-Hydroxyacetophenone-anil compounds such as 4-HAP-anil may be reactive with water and should be kept dry prior to their further use.

In a second step the 4-HAP-anil isolated from the first step is contacted with an acid catalyst, preferably an anilinium salt such as anilinium hydrochloride under suitable reaction conditions to produce the desired 1,3,5-trisaryl benzene product. The mole ratio of anilinium hydrochloride to substituted 4-hydroxyacetophenone-anil is preferably about 0.01:1 to about 0.25:1, more preferably about 0.065:1.0 (or, preferably about 1.0:4.0 to about 1.0:100, more preferably about 1:15). The mole ratios for the two-step process may also be in the ranges described above in connection with the "one step" embodiment of the present invention, for instance ranges of about 1.0:4.0 to 1.0:100, and about 1:10 to about 1:50 such as about 1:12.5 to about 1:25 for the anilinium hydrochloride to 4-hydroxyacetophenone-anil mole ratio.

The reaction conditions of this second step are suitable time and temperature which will not cause significant decomposition of reactants and/or product, and, will obtain a satisfactory yield of the desired product. Reaction times of about 0.25 to about 4 hours and temperatures of about 1800° to about 2200° C. are preferred, e.g., reflux (about 1900° C.) for about 2 hours.

The reaction mixture is cooled and extracted into an aqueous solution, e.g., a basic aqueous solution such as an aqueous alkali hydroxide solution, such as NaOH. When a NAOH solution is used, it may be used in a 1 molar solution (e.g., in small scale 2 g NAOH in 50 ml H$_2$O). Extracting the reaction mixture into an aqueous solution results in a second aqueous solution which is washed with an organic solvent, such as, a relatively non-polar solvent like chloroform (e.g., two times, or in small scale 2×25 ml) and acidified at a pH of, for example, about 6.5 to 3.5, preferably about 5.5 to 4.0, whereby the 1,3,5-tris(4'-hydroxyaryl)benzene precipitates. The solid may be dried, e.g., in a vacuum oven for about 2 to 24 hours at a temperature of about 80 to 120° C. These recovery procedures are not limiting as variations are within the ambit of the skilled artisan. For instance, other aqueous solutions including KOH, Na$_2$CO$_3$ and the like, and, other organic solvents such as methylene chloride and the like can be used.

Examples of 1,3,5-tris(4'-hydroxyaryl)benzenes which can be prepared in accordance with the invention are:

1,3,5-tris(4'-hydroxyphenyl)benzene;
1,3,5-tris(3'-alkyl-4'-hydroxyphenyl)benzene;
1,3,5-tris(3'-halophenyl-4'-hydroxyphenyl)benzene;
1,3,5-tris(3'-nitro-4'-hydroxyphenyl)benzene;
1,3,5-tris(2'-alkyl-4'-hydroxyphenyl)benzene;
1,3,5-tris(2'-alkyl-3'-alkyl 4'-hydroxyphenyl)benzene;
1,3,5-tris(2'-nitro-3'nitro 4'-hydroxyphenyl)benzene; and 1,3,5-tris(2'-halophenyl-3'-halophenyl 4'-hydroxyphenyl)benzene and combinations thereof, e.g. 1,3,5-tris(2'-alkyl-6'-halo-4'-hydroxyphenyl)benzene.

Examples of 4-hydroxyacetophenones used in the reaction are:
4-hydroxyacetophenone;
3-alkyl-4-hydroxyacetophenone;
3-halo-4-hydroxyacetophenone;
3-nitro-4-hydroxyacetophenone;
2-alkyl-4-hydroxyacetophenone;
3-alkyl-4-haloacetophenone; and
2-alkyl-6-halo-4-hydroxyacetophenone.

From the above examples of 1,3,5-tris(4'-hydroxyaryl)benzenes which can be prepared in accordance with the invention, and, the above examples of 4-hydroxyacetophenones used in the reaction, it is to be understood that in the foregoing description terms such as "4-hydroxyacetophenone" and "substituted 4-hydroxyacetophenone" and abbreviations thereof can include both 4-hydroxyacetophenone, i.e., when $R^1$ is hydrogen and x is 1, and substituted 4-hydroxyacetophenones, e.g., when $R^1$ can be other than hydrogen and x is 1 to 4, or when x is greater than 1 and the R' substituents are the same or different and include at least one substituent other than hydrogen. Likewise, in the foregoing description, the terms "1,3,5-tris(4'-hydroxyphenyl)benzene" and "substituted 1,3,5-tris(4'-hydroxyphenyl)benzene" include 1,3,5-tris(4'-hydroxyphenyl)benzene, i.e., when $R^1$ is hydrogen and x is 1 as well as substituted 1,3,5-tris(4'-hydroxyphenyl)benzene, e.g., when $R^1$ is other than hydrogen and x is 1 to 4, or when x is greater than 1 and the $R^1$ substituents are the same or different and include at least one substituent other than hydrogen. And, in this description the terms "1,3,5-trisaryl benzene" and "1,3,5-tris(4'-hydroxyaryl)-benzene" are meant to include both 1,3,5-tris(4'-hydroxyphenyl)benzene and substituted 1,3,5-tris(4'-hydroxyphenyl)benzene.

The inventive method may be further illustrated by the following examples, many apparent variations of which are possible without departing from the spirit and scope thereof.

EXAMPLE 1

One Step Conversion of 4-hydroxyacetophenone to THPB

4-Hydroxyacetophenone (13.6 g, 0.1 mol) was contacted with aniline (18.6 g, 0.2 mol) in the presence of toluene (100 ml; as solvent) and heated to reflux in a round bottom flask equipped with a condenser and a Dean and Stark trap. After most of the 4-HAP was converted to 4-HAP-anil (conversion followed by gas chromatography), anilinium hydrochloride (0.5 g, 0.0038 mol) was added and the toluene was removed via distillation. The reaction mixture was heated at 190°-200° C. for 3 hours, cooled to 120° C. and THPB was recovered as follows. Toluene (100 ml) was added to the cooled reaction mixture and an oil was separated. The supernatant liquid was decanted leaving an oily residue to which was added hexanes (100 ml) to precipitate THPB as a yellow solid (5.3 g). THPB was 88% pure by HPLC analysis.

EXAMPLE 2

Synthesis of THPB via intermediate formation of 4-hydroxyacetophenone (4-HAP) anil Step One: Preparation of 4-HAP-anil 4-Hydroxyacetophenone (27.2 g, 0.2 mol), was contacted with aniline (50 g, 0.54 mol) in the presence of toluene (50 ml) of and heated to reflux in a round bottom flask equipped with a condenser and a Dean and Stark trap. The water from this reaction was collected in the trap. After 17 hours, this reaction mixture was cooled and the 4-HAP-anil was recovered by pouring the cooled reaction mixture into 200 ml of hexanes. A yellowish-brown oily product separated out of the reaction mixture. The oily product was triturated with hexanes (3×200 ml) to afford 45.0 g of a brown solid. Recrystallization of a small sample (5.0 g) with ether/hexane afforded 1.2 g of a yellowish-white solid which by melting point (139°-141° C.) and $^1H$ and $^{13}C$ NMR spectra was determined to be 4-hydroxyacetophenone-anil (4-HAP-anil).

Step Two: THPB from 4-HAP-anil

To a round bottom flask equipped with a magnetic stirrer and a condenser, 4-hydroxyacetophenone-anil (2.5 g, 0.0118 mol) and anilinium hydrochloride (0.1 g, 0.00077 mol) was added. The reaction mixture was heated at reflux (bath temperature 190° C.) for 2 hours, and cooled. THPB was recovered by extracting the reaction mixture into an aqueous 1 molar NAOH solution (2 g NAOH in 50 ml water). The resulting aqueous solution containing extracted reaction mixture was washed with chloroform (2×25 ml) and the chloroform wash was discarded. The aqueous layer was acidified to a pH of 4.0, and the product precipitated as a yellow solid. The solid was dried in a vacuum oven to provide 1.4 g of 84% pure THPB (by HPLC analysis).

EXAMPLE 3

4-HAP to THPB: One Step 4-hydroxyacetophenone (13.6 g) was contacted with (18.6 g) aniline and aniline-HCl (0.5 g) and heated to 185°-190° C. for two hours. A sample was removed from the reaction mixture and by LC analysis determined to be 31% 4-HAP and 67.5% THPB. Heating at 185°-190° C. continued for another two hours and thereafter a sample was removed from the reaction mixture. By LC analysis, the reaction mixture after four hours was 23% 4-HAP and 75% THPB. 10 ml of toluene was then added to the reaction mixture and heating at 190°-200° C. was continued for about another 2 hours. A sample was then analyzed by LC analysis and determined to be 6% 4-HAP and 93% THPB.

Heating was continued until most of the aniline was distilled out. The THPB was recovered by pouring the reaction mixture after the aniline distillate was distilled out into dilute $H_2SO_4$ and extracting with ethyl acetate. The ethyl acetate was washed with water and product was crystallized to yield (by LC analysis) 95% 4-HAP-trimer (THPB).

This Example demonstrates that the use of toluene solvent is optional, but preferred.

EXAMPLE 4

4-HAP to THPB: One Step

A reaction mixture of 4-hydroxyacetophenone (13.6 g), aniline (28.0 g) and aniline HCl (1.0 g) was heated to 220° C. in a reaction flask fitted with a Dean and Stark trap filled with 90% aniline and stirred for 4 hours at that temperature. The reaction mixture was cooled to room temperature and the THPB was recovered by pouring the cooled reaction mixture into a dilute sodium hydroxide solution (12.0 g NAOH in 200 ml $H_2O$), separating out the aniline and washing the aqueous solution with chloroform. The aqueous layer was acidified, with drops of dilute HCl, to a pH of about 5.5, and a solid was precipitated. The precipitated solid was collected via filtration and dried in a vacuum oven to yield 10.8 g. Using $^1H$ and $^{13}C$ NMR and LC analyses, the product was 48% pure. Recrystallization would produce a more purified product.

EXAMPLE 5

4-HAP to 4-HAP-anil

A reaction mixture of 4-hydroxyacetophenone (27.2 g) and aniline (50.0 g) in toluene (100 ml.) as solvent was mixed in a two-necked 500 ml flask equipped with a Dean and Stark trap and a condenser and heated to reflux using an oil bath at about 180° C. for 16 hours. Samples were withdrawn at 4, 12, and 16 hours and analyzed by Gas Chromatography. After 4 hours there was 50% conversion to 4-HAP-anil; after 12 hours there was 80% conversion to 4-HAP-anil; and, after 16 hours there was 88% conversion to 4-HAP-anil. After 16 hours, the reaction mixture was cooled, petroleum ether was added and an oily layer separated in the bottom. The oily layer was triturated with petroleum ether to give a thick pasty oil which was dissolved in chloroform. The addition of petroleum ether resulted in a reddish brown solid. Gas Chromatography on a sample of this solid showed it to be 80% imine (4-HAP-anil), 6% 4-HAP, and 4.5% aniline. 5.0 grams of the solid was recrystallized with chloroform/hexane to give a yellow solid which was 96% pure 4-HAP-anil by Gas Chromatographic analysis. It was also observed that the 4-HAP-anil was reactive with water. A sample of 4-HAP-anil left in an open flask overnight hydrolyzed to 4-HAP and aniline as determined by Gas Chromatography. Thus, the imine was kept dry prior to its use in making THPB.

EXAMPLE 6

THPB from 4-HAP-anil

In a flask, 4-hydroxyacetophenone-aniline imine (4-HAP-anil) (2.11 g; 0.01 mol) was heated at about 190°C for 0.5 hours in the presence of about 0.1 g anilinium hydrochloride. The flask was cooled and the product was dissolved in dilute aqueous sodium hydroxide, and the aqueous solution was washed with chloroform. The aqueous layer was separated and acidified slowly by the addition of dilute HCl until obtaining a pH of about 4.0. A yellow solid precipitated which was collected via filtration, air dried and then dried in an oven at about 70° C. and a pressure of about 50 mm Hg. The resultant solid weighed 1.18 g and, by analysis, was 71.4% THPB and 0.6% 4-HAP.

EXAMPLE 7

THPB from 4-H&P-anil

Step two of Example 2 was repeated, except that the reaction mixture was refluxed for 4 hours. THPB was recovered as set out in step two of Example 2 to provide 1.4 g of 75% pure THPB (by $^{13}C$ and $^1H$ NMR and HPLC analyses).

Having described in detail preferred embodiments of the present invention, it is to be understood that the invention defined by the claims is not to be limited by particular details set forth in the description as many apparent variations are possible without departing from the spirit of the present invention.

What is claimed is:

1. A process for preparing a 1,3,5-tris(4'-hydroxyaryl)benzene compound of formula (I):

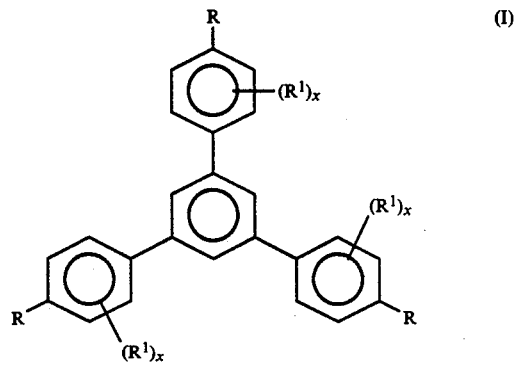

wherein R is hydroxy, $R^1$ is hydrogen, $C_1$-$C_{12}$ alkyl, $C_3$-$C_6$ cycloalkyl, phenyl, halogen, nitro, or alkyl or aromatic sulfonyl, x is an integer from 1 to 4, and when x is greater than 1 each $R^1$ thereof can be the same or different, said process comprising reacting a substituted 4-hydroxyacetophenone-anil compound of formula (III):

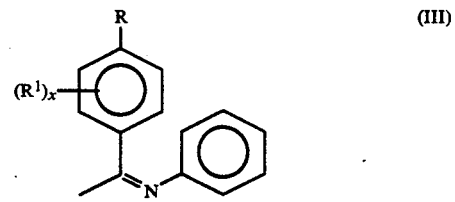

wherein R, $R^1$ and x are as defined above, with an acid catalyst at about 150°-220° C. for about 0.25 to about 4 hours with water being continuously removed from the reaction, wherein compound III is present in at least three molar ratio quantities and is kept substantially anhydrous prior to said reaction, wherein said acid catalyst is present in a molar ratio range of about 1:4 to about 1:100 with respect to compound III, and wherein said catalyst is a salt of aniline or naphthylamine with said aniline or naphthylamine being substituted or unsubstituted in its aromatic ring, said substituents being selected from the group consisting of a $C_1$-$C_6$ alkyl, $C_1$-$C_6$ alkoxy and halo groups.

2. The process of claim 1 wherein the acid catalyst is anilinium hydrochloride.

3. The process of claim 1 wherein x is 1 and $R^1$ is hydrogen.

4. The process of claim 2 wherein x is 1 and $R^1$ is hydrogen.

5. The process of claim 4 wherein the mole ratio of anilinium hydrochloride compound of formula (III) is about 1.0:12.5 to about 1.0:25.

6. The process of claim 4 wherein the reaction conditions include temperature ranging from about 185° to about 200° C. and time ranging from about 0.25 to about 2 hours.

7. The process of claim 1 wherein the acid catalyst is naphthylaminium hydrochloride.

8. A process for preparing a 1,3,5-tris(4'-hydroxyaryl)benzene compound of formula (I):

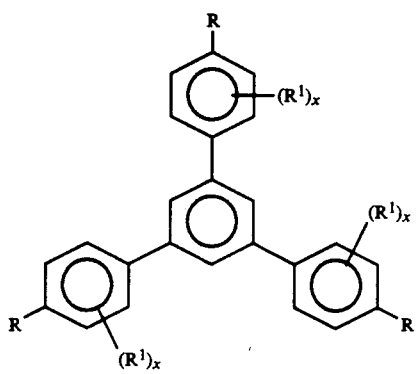

wherein R is hydroxy, $R^1$ is hydrogen, $C_1$-$C_{12}$ alkyl, $C_3$-$C_6$ cycloalkyl, phenyl, halogen, nitro, or alkyl or aromatic sulfonyl, x is an integer from 1 to 4, and when x is greater than 1, each R' thereof can be the same or different, said process comprising: (i) reacting a substituted 4-hydroxyacetophenone compound of formula (II):

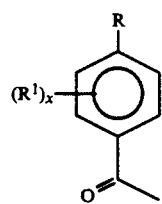

wherein R, $R^1$ and x are as defined above, at about 80°-160° C. for about 2-24 hours, with a substituted or unsubstituted aniline derivative, said substituents being on the aromatic ring and being selected from the group consisting of a $C_1$-$C_6$ alkyl, $C_1$-$C_6$ alkoxy and halo groups, wherein said compound II is present in at least three molar ratio quantities, and wherein said aniline derivative is present in a molar ratio range of about 1:1 to about 10:1 with respect to compound II, whereby a substituted 4-hydroxyacetophenone-anil compound of formula (III)

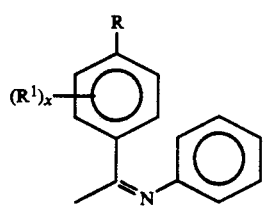

wherein R, $R^1$ and x are as defined above, is formed, and (ii) reacting said compound of formula (III) with an acid catalyst at about 150°-220° C. for about 0.25 to about 4 hours, with water being continuously removed from the reaction of step (ii), wherein said compound III is kept substantially anhydrous prior to said reaction of step (ii), wherein said acid catalyst is present in a molar ratio range of about 1:4 to about 1:100 with respect to compound III, and wherein said catalyst is a salt of aniline or naphthylamine with said aniline or naphthylamine being substituted or unsubstituted in its aromatic ring, said substituents being selected from the group consisting of a $C_1$-$C_6$ alkyl, $C_1$-$C_6$ alkoxy and halo groups.

9. The process of claim 8 wherein said aniline derivative in step (i) is aniline and said acid catalyst in step (ii) is anilinium hydrochloride.

10. The process of claim 8 wherein x is 1 and $R^1$ is hydrogen.

11. The process of claim 9 wherein x is 1 and $R^1$ is hydrogen.

12. The process of claim 8 wherein step (i) is without isolation of compound of formula (III).

13. The process of claim 8 wherein said reaction of step (i) is performed at about 1500 to about 180° C. for about 2-17 hours, and said reaction of step (ii) is performed at temperature ranging from about 185° to about 200° C. and time ranging from about 0.5 to about 2 hours.

14. The process of claim 8 wherein the mole ratio of said aniline derivative to the compound of formula (II) in step (i) is about 1:1 to about 2:1 and the mole ratio of said acid catalyst to the compound of formula (III) in step (ii) is about 1:12.5 to about 1:25.

15. The process of claim 14 wherein step (i) includes adding a solvent.

16. The process of claim 8 wherein step (i) includes adding a solvent.

17. The process of claim 15 or claim 16 wherein said solvent is a non-polar organic solvent.

18. The process of claim 8 wherein step (i) includes isolating compound of formula (III).

19. A process for preparing a 1,3,5-tris(4'-hydroxyaryl)benzene compound of formula (I)

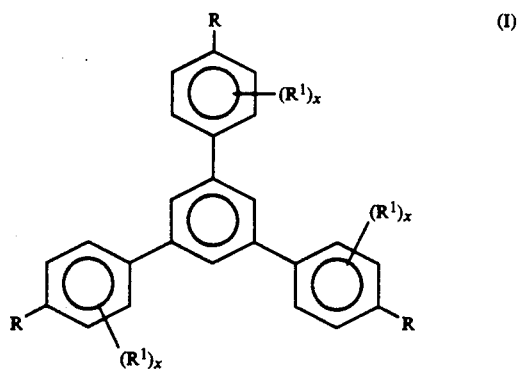

wherein R is hydroxy, $R^1$ is hydrogen, $C_1$-$C_{12}$ alkyl, $C_3$-$C_6$ cycloalkyl, phenyl, halogen, nitro, or alkyl or aromatic sulfonyl, x is an integer from 1 to 4, and when x is greater than 1, each $R^1$ thereof can be the same or different, said process comprising reacting a substituted 4-hydroxyacetophenone compound of formula (II)

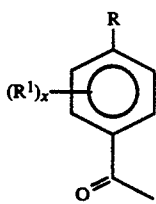

(II)

wherein R, R¹ and x are as defined above, wherein said compound II is present in at least three molar quantities, with a substituted or unsubstituted aniline derivative, said substituents being on the aromatic ring and being selected from the group consisting of a $C_1$–$C_6$ alkyl, $C_1$–$C_6$ alkoxy and halo groups, said aniline being present in a molar ratio range of about 1:1 to about 10:1 with respect to compound II, at about 150° to about 220° C, for about 0.5 to about 8 hours, in the presence of an acid catalyst at about 150°–220° C. for about 0.25 to about 4 hours, wherein said acid catalyst is present in a molar ratio range of about 1:4 to about 1:100 with respect to compound III, and wherein said catalyst is a salt of aniline or naphthylamine with said aniline or naphthylamine being substituted or unsubstituted in its aromatic ring, said substituents being selected from the group consisting of a $C_1$–$C_6$ alkyl, $C_1$–$C_6$ alkoxy and halo groups.

20. The process of claim 19 wherein said acid catalyst is anilinium hydrochloride.

21. The process of claim 19 wherein x is 1, and R¹ is hydrogen.

22. The process of claim 19 wherein the reaction conditions include temperatures ranging from about 185° to about 220° C. and times ranging from about 0.5 to about 6 hours.

23. The process of claim 20 wherein the mole ratio of aniline derivative to the compound of the formula (II) is about 1:1 to about 2:1 and the mole ratio of anilinium hydrochloride to the compound of the formula (II) is about 1:12.5 to 1:25.

24. The process of claim 19 further comprising adding a solvent.

* * * * *